United States Patent [19]

Khouw et al.

[11] 4,065,355

[45] Dec. 27, 1977

[54] PURIFICATION OF DEOXYRIBONUCLEASE

[75] Inventors: Boen Tie Khouw, Islington; Johan Peter Kesler, Rexdale, both of Canada

[73] Assignee: Canada Packers Limited, Toronto, Canada

[21] Appl. No.: 730,739

[22] Filed: Oct. 8, 1976

Related U.S. Application Data

[63] Continuation of Ser. No. 561,921, March 25, 1975, abandoned.

[51] Int. Cl.² .................. C07G 7/02; C07G 7/026
[52] U.S. Cl. .................................. 195/66 R; 195/63; 195/68
[58] Field of Search .......... 195/66 R, 63, 68, DIG. 11

[56] References Cited

U.S. PATENT DOCUMENTS 3,836,433 9/1974 Wirth et al. ............................ 195/68

OTHER PUBLICATIONS

Avrameas et al., Biologically Active Water-Insoluble Protein Polymers, Their Use for the Isolation of Specifically Interacting Proteins, Biochimie, vol. 53, 1971 (pp. 603-614).

Murthy, et al., Purification of Human & -Antitrypsin by Affinity Chromatography on Sepharose Bound Concenavalina, Febs. Letters, vol. 32, No. 2, 1973, (pp. 243-246).

Fletcher, et al., Protection of Deoxyribonuclease from Ionizing Radiation by Adsorbents, Nature vol. 176, 1955, (pp. 882-883).

Zaborsky, O., Immobilized Enzymes, CRC Press, Cleveland, Ohio, 1973, (pp. 28-32 & 79).

*Primary Examiner*—David M. Naff
*Attorney, Agent, or Firm*—Bacon & Thomas

[57] ABSTRACT

Highly purified deoxyribonuclease is obtained by a simple process which comprises adsorption of deoxyribonuclease from a crude or partially purified solution of the enzyme on a column of concanavalin A-agarose, followed by elution of the adsorbed deoxyribonuclease with a carbohydrate solution and recovery of the deoxyribonuclease in solid form from such solution.

5 Claims, No Drawings

PURIFICATION OF DEOXYRIBONUCLEASE

This is a continuation, of application Ser. No. 561,921, filed Mar. 25, 1975, and now abandoned.

BACKGROUND OF THE INVENTION

This invention relates to the isolation and purification of deoxyribonuclease from crude or partially purified preparations of the enzyme. Deoxyribonuclease enzymes, hereinafter termed "deoxyribonuclease" or "DNase", are widely distributed in nature and are present in substantial amounts in the pancreas, blood and spleen of animals as well as in yeasts. A good source of deoxyribonuclease is the bovine pancreas, however, porcine pancreas and bovine spleen may also serve as source materials.

Deoxyribonuclease has several medicinal and veterinary uses. One use is as a debriding agent to liquefy pus in order to aid in the removal of necrotic debris from skin surfaces.

Numerous methods are described in the literature for the isolation and purification of DNase from bovine pancreas. The enzyme is customarily extracted into dilute sulfuric acid, followed by a series of ammonium sulfate fractionations, heat treatment, alcohol fractionation and ammonium sulfate crystallization at acidic pH. The yield of crystalline DNase is in the order of 3-5 mg/kg pancreas, and it is often contaminated with large amounts of chymotrypsin B or its zymogen. A modified sulfuric acid extraction procedure, purported to give higher yields (2-3 times as much) of crude DNase/kg pancreas is disclosed in U.S. Pat. No. 2,801,956.

Other methods for obtaining highly purified deoxyribonuclease involve electrodecantation, chromatography on either cation exchangers or anion exchangers, and affinity chromatography on agarose-bound DNA. While the foregoing methods have been reported to yield highly pure deoxyribonuclease, the starting materials were either purified (70% pure) or crystalline enzyme. Furthermore, treatment of these starting materials with a highly toxic proteolytic enzyme inhibitor, such as diisopropylfluorophosphate (DFP) was always necessary to ensure a recovery of purified enzyme greater than 50%. Of the foregoing methods, affinity chromatography on a column of agarosebound DNA appears to be the most selective and simple. However, this method has the disadvantage of having a low column capacity when a crude enzyme source is used as a starting material in the purification process.

SUMMARY OF THE INVENTION

This invention provides a relatively simple process for the isolation and purification of deoxyribonuclease from either a crude enzyme material or partially purified enzyme material to provide a highly purified deoxyribonuclease product in good yield.

Briefly, the process comprises contacting a solution of the enzyme material with a solution of concanavalin A to form an insoluble deoxyribonuclease-concanavalin A complex, isolating the complex and dissociating this complex with a carbohydrate solution. This procedure is based on the premise that deoxyribonuclease is a glyco-protein containing carbohydrate residues, mannosyl and glucosyl, which will interact with concanavalin A, a Jack Bean lectin, to form an insoluble complex. However, the invention is not intended to be limited by any particular theory of operation. It has been discovered, pursuant to this invention, that deoxyribonuclease forms an insoluble complex and is bound to concanavalin A to a sufficient degree that any impurities present may be readily removed by washing and that thereafter, deoxyribonuclease may be almost quantitatively recovered. In the presence of a suitable carbohydrate solution dissociation readily takes place.

Crude extracts of deoxyribonuclease, from for example bovine pancreas, contain proteolytic enzymes such as trypsin and chymotrypsin which readily inactivate deoxyribonuclease in the absence of the divalent metal cation of calcium. We have found that the presence of calcium ion in the enzyme solution is useful for optimum binding of deoxyribonuclease to concanavalin A, and therefore is preferably present throughout the process.

In order to facilitate the recovery of the enzyme and to conserve concanavalin A, it is preferred to use an insoluble form of the lectin for adsorption of deoxyribonuclease from solution. Thus, the lectin may be coupled to an insoluble matrix such as agarose. Such materials are well known in the art. A representative commercial material, suitable for purposes of this invention, is available under the tradename Concanavalin A-Sepharose from Pharmacia of Uppsala, Sweden. This may be used in the form of a column with the procedural steps of adsorption, washing and elution. Elution of the deoxyribonuclease from the column is carried out by washing the column with an appropriate carbohydrate solution. The eluate containing purified deoxyribonuclease may then be recovered in solid form by first dialyzing the solution to remove any lowmolecular weight carbohydrates, and thereafter freeze-drying the solution, or by any other suitable means.

Comparison of solid deoxyribonuclease product purified by the present method as compared with crystalline deoxyribonuclease obtained by the standard Kunitz method (J. Gen. Physiol. 1950, 33, 349), has shown the enzymes to be electrophoretically similar but the product of the present method shows a much high potency (over 2000 DNase units per mg).

DETAILED DESCRIPTION OF THE INVENTION

A preferred overall embodiment of the invention comprises treating animal pancreas by known methods to provide a crude or partially purified deoxyribonuclease material, such as an ammonium sulfate precipitate of a sulfuric acid extract, forming a solution of this source material at a pH in the range of about 3.5 to 9.0 with a buffer containing calcium ions, adsorbing deoxyribonuclease from said buffered solution on a column comprising concanavalin A-agarose, washing the column with the buffer to remove unadsorbed or loosely bound impurities from the complex, eluting the deoxyribonuclease from the column with a dilute solution of a carbohydrate in the same buffer, and recovering purified deoxyribonuclease in solid form from the eluate.

While the operable pH range is broad, pH does affect the capacity of deoxyribonuclease to adsorb onto a concanavalin Aagarose column. This is illustrated by Table I below. In a pH range of 4.0 to 9.0 a Concanavalin A-Sepharose column exhibits an approximately equivalent capacity to adsorb deoxyribonuclease. At about a pH of 3.5 adsorption is reduced about half, while below a pH of 3.5 and higher than a pH of 9.0, the Concanavalin A-Sepharose affinity gel is not stable. Desorption with carbohydrate solution is accomplished in the same general pH range.

The carbohydrates useful for this invention are those which interact with concanavalin A and in general comprise monosaccharides, polysaccharides, carbohydrate acetals and amino sugars.

TABLE I

Adsorption Capacity of Concanavalin A-Sepharose, 8 mg concanavalin A/ml (Pharmacia)

| pH | DNase Units Adsorbed/ml ConA-Seph. |
|---|---|
| 3.5 | 7,500 |
| 4.0 | 14,600 |
| 5.0 | 15,500 |
| 6.0 | 16,000 |
| 7.0 | 14,500 |
| 8.0 | 16,000 |
| 9.0 | 16,000 |

It has also been determined that within the useful range of hydrogen ion concentrations, the adsorption capacity of the Concanavalin A-Sepharose column, while dependent on the purity of deoxyribonuclease starting material, is good even for materials of relatively low purity. This is illustrated by Table II below:

TABLE II

ISOLATION AND PURIFICATION OF DEOXYRIBONUCLEASE

| Specific Activity (units/mg) | DNase Adsorbed/ml ConA-Seph. (mg) | (Percentage) |
|---|---|---|
| 3800 | 4.90 | 100 |
| 2000 | 4.53 | 93 |
| 444 | 3.74 | 76 |
| 147 | 2.45 | 50 |
| 96 | 1.74 | 36 |

It has been found that substantially any carbohydrate or its derivative capable of interaction with the concanavalin A is suitable for displacing deoxyribonuclease from a concanavalin A-agarose column. Table III shows the effects of representative carbohydrates and their derivatives on elution, when tested at a concentration of about 2% (weight/volume).

TABLE III

Effect of Solutions of Various Carbohydrates (2%) for Eluting DNase Adsorbed to One Milliliter of Concanavalin A-Sepharose at pH 6.0

| Carbohydrates | mg DNase Eluted from 1 ml ConA-Seph. |
|---|---|
| a-Methylmannoside (MM) | 4.3 |
| a-Methylglucoside (MG) | 3.9 |
| Mixture of MM & MG (1%) | 4.7 |
| Mannose | 4.1 |
| Sucrose, maltose, sorbose, salicin, sedoheptulose, glucose, fructose, N-acetyl-glucosamine | 3.3 – 3.8 |
| Isomaltose (0.25%), glucosamine, galactose, erythrose | 2.2 – 2.8 |
| Xylose, arabinose, fucose, ribose, lactose, sorbitol, cellobiose, rhamnose, raffinose, glycogen (1%), inositol, mannitol | 1.5 – 1.9 |

The concentration of carbohydrate in the eluting solution is not sharply critical. The minimum concentration for elution with a-methylmannoside at pH 6 is about 0.0001 molar. As a practical matter carbohydrate solutions of about 0.01 to 1 molar are preferred. However, it will be understood that this is not a critical range and that one can readily determine the optimum concentration for the selected carbohydrate.

The process of the invention for purifying deoxyribonuclease from either a crude or partially purified source is represented by the following:

INTERACTION OF DNASE AND CONCANAVALIN A

In solutions, DNase interacts with Concanavalin A to form an insoluble complex. In the presence of a suitable carbohydrate, the complex is readily solubilized and dissociated. The individual components are then recoverable by means of cation-exchange chromatography as illustrated in the following example.

EXAMPLE I

Concanavalin A (24 mg) was added to a solution of DNase containing a total of 168,000 units at 25° C, pH 6.0 (1M NaCl, 0.1 M sodium acetate, 0.01 M calcium acetate, 0.001 M EDTA). After 10 minutes, the insoluble complex was recovered by centrifugation and dissolved in 10% a-methylmannoside in a buffer of pH 4.5 (0.05 M NaCl, 0.1 M sodium formate, 0.01 M calcium formate). Following dialysis against the same mannoside buffer, the dialyzed solution (100,000 units) was applied onto a column of sulfoethylSephadex (Pharmacia) previously equilibrated with the same mannoside buffer at pH 4.5. While Concanavalin A was retained by the cation exchanger, DNase passed through unretarded and was recovered from the wash.

In order to facilitate the recovery of enzyme and to conserve Concanavalin A, an insoluble form of the lectin is preferably used for the adsorption of DNase from solutions. This is illustrated by the following example.

EXAMPLE II

A crude deoxyribonuclease is obtained as an ammonium sulfate precipitate of beef pancreatic extract as described by Kunitz (J. Gen. Physiol, 1950, 33, 349). According to this procedure, fresh beef pancreas is placed in an ice cold 0.25 N sulfuric acid solution. The pancreas are then drained of acid, cleaned of fat and connective tissue and coarsely ground. The ground pancreas is suspended in an approximately equal volume of ice cold distilled water and a quantity of the cold 0.25 N sulfuric acid is added to lower the pH of the fluid in the suspension to about 3.0 (This normally requires a volume of 0.25 N acid equal to about half of the water added). The resulting pancreas suspension is stored at approximately 5° C for 18 to 20 hours and then strained through cheese cloth. The residue is resuspended in ice cold water and strained for a second time. The filtrates are combined and brought to 0.2 saturation of ammonium sulfate by addition of approximately 114 grams of the salt per line of filtrate solution. The resulting precipitate is separated by filtration and removed. The clear filtrate is re-saturated with ammonium sulfate to 0.4 saturation to precipitate deoxyribonuclease.

The crude deoxyribonuclease precipitate obtained by the aforementioned Kunitz procedure is dissolved in a buffer consisting of 1M sodium chloride (NaCl), 0.1sodium acetate, 0.01M calcium acetate and 0.001M EDTA at a pH of 6.0. Following clarification, the clear solution at a pH of 6.0 is applied to a column of Concanavalin A bound agarose previously equilibrated with the same buffer. Unadsorbed components are removed from the column by washing with the buffer solution and the adsorbed deoxyribonuclease is eluted with a 2% solution of α-methylmannoside prepared in the same buffer.

The following Table IV illustrates the purification of deoxyribonuclease from two source materials of different DNase concentration by the foregoing method.

TABLE IV

Purification of DNase on a One-liter column of Concanavalin A-Sepharose (8-mg Concanavalin A/ml. Pharmacia), at pH 6.0

| Fraction | Protein (g) | Total Acitivity (units) | Specific Activity (units/mg) |
|---|---|---|---|
| Sample 1: | | | |
| Solution of Crude DNase | 182 | $15.1 \times 10^6$ | 83 |
| DNase not adsorbed | | $4.5 \times 10^6$ | |
| DNase adsorbed (by difference) | | $10.6 \times 10^6$ | |
| Mannoside Eluate | 3.7 | $8.8 \times 10^6$ | 2395 |
| Sample 2: | | | |
| Solution of Crude DNase | 58.8 | $27.0 \times 10^6$ | 459 |
| DNase not adsorbed | | $4.3 \times 10^6$ | |
| DNase adsorbed (by difference) | | $22.7 \times 10^6$ | |
| Mannoside Eluate | | $18.6 \times 10^6$ | 3320 |
| Ammonium sulfate precipitate | | $15.7 \times 10^6$ | 3651 |
| Lyophilized Powder, DNase | 4.2 | $15.3 \times 10^6$ | 3643 |

At least 80% of the adsorbed DNase from these samples was recovered in the mannoside eluate. Following the usual ammonium sulfate precipitation, desalting and lyophilization, a highly purified DNase (>3500 units/mg) was obtained. Electrophoretically, the enzyme so obtained was similar to the crystalline DNase (assaying at 2000 units/mg) prepared by the standard Kunitz method. Furthermore, the method of this invention was found to be capable of yielding DNase with an overall recovery of greater than 60% from beef pancreas.

It should be understood that the invention is not to be limited to the exact details of operation as herein described, and the invention is therefore to be limited only by the scope of the appended claims.

We claim:

1. A process for the preparation of purified deoxyribonuclease from an impure source material thereof comprising, dissolving an impure deoxyribonuclease material in a buffer solution having a pH between about 3.5 and 9.0 and containing calcium ions, clarifying the resulting solution, applying the clarified solution to a column consisting essentially of concanavalin A chemically bound to agarose, the purity of the deoxyribonuclease in said solution being sufficiently high that there is substantial adsorption of deoxyribonuclease on the column, washing said column with buffer solution to remove impurities more loosely bound than deoxyribonuclease, eluting the adsorbed deoxyribonuclease from the column by contacting it with a carbohydrate solution, and recovering a purified deoxyribonuclease from said carbohydrate solution.

2. The process of claim 1, wherein said carbohydrate solution is selected from at least one carbohydrate from the group consisting of monosaccharides and polysaccharides.

3. The process of claim 1, wherein said carbohydrate solution is a dilute solution of α-methylmannoside.

4. The process of claim 1, wherein the buffer comprises NaCl, sodium and calcium acetates and ethylenediamine tetraacetic acid and has a pH of about 6.0.

5. A process for the isolation and purification of deoxyribonuclease, comprising extracting deoxyribonuclease from animal pancreas; precipitating deoxyribonuclease from said extract with ammonium sulfate; preparing a solution of said precipitated deoxyribonuclease having a pH between about 3.5 and about 9.0 and containing calcium ions; clarifying said solution; adsorbing deoxyribonuclease from said clarified solution on a column consisting essentially of Concanavalin A chemically bound to agarose; eluting said adsorbed deoxyribonuclease from said column by contacting said column with a solution of at least one carbohydrate selected from the group consisting of monosaccharides and polysaccharides; and recovering purified deoxyribonuclease in solid form from the eluate.

* * * * *

UNITED STATES PATENT OFFICE
CERTIFICATE OF CORRECTION

Patent No. 4,065,355                    Dated December 27, 1977

Inventor(s) BOEN TIE KHOUW and JOHAN PETER KESLER

It is certified that error appears in the above-identified patent and that said Letters Patent are hereby corrected as shown below:

Column 3, line 52, change "crythrose" to --erythrose--;

line 55, change "(1%)" to --(0.1%)--.

Column 4, line 60, change "0.1sodium acetate" to

--0.1M sodium acetate--.

Signed and Sealed this

Ninth Day of May 1978

[SEAL]

Attest:

RUTH C. MASON
Attesting Officer

LUTRELLE F. PARKER
Acting Commissioner of Patents and Trademarks